United States Patent [19]

Pugin et al.

[11] Patent Number: 5,011,995
[45] Date of Patent: Apr. 30, 1991

[54] PROCESS FOR THE PREPARATION OF OPTICALLY ACTIVE SECONDARY AMINES

[75] Inventors: Benoit Pugin, Münchenstein; Gerardo Ramos, Arlesheim; Felix Spindler, Starrkirch-Wil, all of Switzerland

[73] Assignee: Ciba-Geigy Corporation, Ardsley, N.Y.

[21] Appl. No.: 221,403

[22] Filed: Jul. 19, 1988

[30] Foreign Application Priority Data

Jul. 28, 1987 [CH] Switzerland ......................... 2870/87

[51] Int. Cl.$^5$ ............................................. C07C 209/88
[52] U.S. Cl. .................................... 564/302; 546/147; 548/470; 558/354; 560/43; 562/457; 564/303; 564/304
[58] Field of Search ........................ 564/302, 303, 304; 562/457; 560/43; 558/354; 548/470; 546/147

[56] References Cited

U.S. PATENT DOCUMENTS 2,608,583  8/1952  Aschner ............................... 564/302
4,187,313  2/1980  Gschwend et al. ............. 564/304 X
4,556,740  12/1985  Hansen et al. ......................... 568/13

FOREIGN PATENT DOCUMENTS 0104375  4/1984  European Pat. Off. .

OTHER PUBLICATIONS

"Organic Chemistry", 3rd Ed. pp. 636–637 (1973), Morrison et al.
Asymmetric Synthesis, vol. 5, pp. 13–23, (Academic Press, Inc.,), N.Y. (1985).
Inorganic Chemica Acta, p. 275 (1983).
J. of Organomet. Chem., 114, pp. 225–232 (1976).
J. Chem. Soc. (A), p. 2334 (1971).
J. of Molecular Catalysis, 22, pp. 283–287 (1984).

*Primary Examiner*—Richard L. Raymond
*Attorney, Agent, or Firm*—Stephen V. O'Brien; Michael W. Glynn

[57] ABSTRACT

Asymmetric hydrogenation of prochiral N-aliphatic ketimines to give optically active secondary amines at a temperature from $-20°$ to $80°$ C., a hydrogen pressure of $10^5$ to $10^7$ Pa, with the addition of catalytic amounts of an iridium compound of the formula III or IIIa $$[XIrYZ] \qquad (III)$$

or $$[XIrY]^{\oplus}A^{\ominus} \qquad (IIIa)$$

in which X is two olefin ligands or a diene ligand, Y is a chiral diphosphine the secondary phosphine group of which are attached through 2–4 C atoms and which, together with the Ir atom, forms a 5-membered, 6-membered or 7-membered ring, or Y is a chiral diphosphinite the phosphinite groups of which are attached via 2 C atoms and which, together with the Ir atom, forms a 7-membered ring, Z is Cl, Br or I and $A^-$ is the anion of an oxygen acid or complex acid, and, if appropriate, with the addition of an ammonium chloride, bromide or iodide or an alkali metal chloride, bromide or iodide.

11 Claims, No Drawings

PROCESS FOR THE PREPARATION OF OPTICALLY ACTIVE SECONDARY AMINES

The present invention relates to a process for the preparation of optically active secondary amines by asymmetric hydrogenation of prochiral N-aliphatic ketimines by means of chiral iridium diphosphine or diphosphinite complexes.

EP-A 0,104,375 describes chiral diphosphine ligands the complexes of which with metals of group VIII of the periodic system can be used as catalysts in the asymmetric hydrogenation of α-(acylamine)-acrylic acids.

L. Marko et al. describe, in J. Mol. Catal. 22, pages 283–287 (1984) and J. Organomet. Chem. 279, pages 23–29 (1985), the asymmetric hydrogenation of N-benzyl phenyl methyl ketimine by means of rhodium complexes of chiral diphosphines or diphosphinites. The chemical activity of the complexes is low and, moreover, the optical yields which can be achieved are not always reproducible.

It has been found that iridium compounds containing chiral diphosphine or diphosphinite ligands are suitable homogeneous, asymmetric catalysts for the hydrogenation of prochiral N-aliphatic ketimines. This reaction results, under a lower pressure and at high chemical conversions and good optical yields, in optically active secondary amines which, surprisingly, do not act as a catalyst poison in spite of their strong basicity and nucleophilic character. Optically active means an excess of one enantiomer having the R or S configuration.

The present invention relates to a process for the preparation of optically active secondary N-aliphatic amines of the formula I

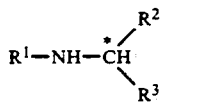
(I)

in which R1 is linear or branched $C_1$–$C_{12}$alkyl, cycloalkyl having 3 to 8 ring C atoms, heterocycloalkyl which is linked via a C atom and has 3 to 8 ring atoms and 1 or 2 heteroatoms selected from the group consisting of O, S and $NR^4$, a $C_7$–$C_{16}$aralkyl which is attached via an alkyl C or $C_1$–$C_{12}$alkyl which is substituted by the cycloalkyl or heterocycloalkyl or heteroaryl mentioned each of which can be unsubstituted or substituted by $C_1$–$C_{12}$ alkyl, $C_1$–$C_{12}$alkoxy, $C_1$–$C_{12}$alkylthio, $C_1$–$C_6$-halogenoalkyl, halogen, —OH—, —CN, $C_6$–$C_{12}$aryl, $C_6$–$C_{12}$aryloxy, $C_6$–$C_{12}$arylthio, $C_7$–$C_{16}$aralkyl, $C_7$–$C_{16}$aralkoxy or $C_7$–$C_{16}$aralkylthio, it being possible for the aryl radicals in turn to be substituted by $C_1$–$C_4$—alkyl, $C_1$–$C_4$alkoxy, $C_1$–$C_4$alkylthio, halogen, —OH, —CN, —$CONR^4R^5$ or —$COOR^4$, secondary amino having 2 to 24 C atoms,

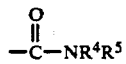

or —$COOR^4$, $R^5$ being H or independently being as defined for $R^4$ and $R^4$ being $C_1$–$C_{12}$alkyl, phenyl or benzyl, or $R^4$ and $R^5$ together being tetramethylene, pentamethylene or 3-oxapentylene; $R^2$ and $R^3$ are different from one another and are $C_1$–$C_{12}$alkyl which is unsubstituted or substituted by —OH, —CN, halogen, $C_1$–$C_{12}$alkoxy, phenoxy, benzyloxy, secondary amino having 2 to 24 C atoms,

or —$COOR^4$, or are cycloalkyl having 3–8 ring C atoms, $C_6$–$C_{12}$aryl which is unsubstituted or substituted as above for $R^1$ where the latter is aralkyl and aryl, or $C_7$–$C_{16}$aralkyl or —$CONR^4R^5$ or —$COOR^4$ in which $R^4$ and $R^5$ are as defined above; or $R^1$ is as defined above and $R^2$ and $R^3$ together are alkylene which has 2 to 5 C atoms and is, if appropriate, interrupted by 1 or 2 —O—, —S— or —$NR^4$— groups, and/or is unsubstituted or substituted by =O or as above for $R^2$ and $R^3$ when the latter are alkyl, and/or is condensed with benzene, furan, thiophene or pyrrole which is unsubstituted or substituted as mentioned above for the aryl radicals, or $R^2$ is as defined above and $R^1$ and $R^3$ together are alkylene which has 2 to 5 C atoms and is, if appropriate, interrupted by 1 or 2 or —O—, —S— or —$NR^4$— groups, and/or is unsubstituted or substituted by =O or as above for $R^2$ and $R^3$ when the latter are alkyl, and/or is condensed with benzene, furan, thiophene or pyrrole which is unsubstituted or substituted as defined above, and * is predominant R-configuration or S-configuration, by the asymmetric catalysed hydrogenation of prochiral ketimines of the formula II

(II)

in which $R^1$, $R^2$ and $R^3$ are as defined above, in the presence of complex salts of a noble metal having chiral ligands, which comprises carrying out the hydrogenation at a temperature from −20° to 80° C. and under a hydrogen pressure from $10^5$ Pa to $10^7$ Pa and adding to the reaction mixture catalytic amounts of an iridium compound of the formula III or IIIa

(III)

or

(IIIa)

in which X is two olefin ligands or a diene ligand, Y is a chiral diphosphine the secondary phosphine groups of which are attached through 2–4 C atoms and which, together with the Ir atom, forms a 5-membered, 6-membered or 7-membered ring, or Y is a chiral diphosphinite the phosphinite groups of which are attached via 2 C atoms and which, together with the Ir atom, forms a 7-membered ring, Z is Cl, Br or I and A⊖ is the anion of an oxygen acid or complex acid.

$R^1$ can be substituted in any desired positions by identical or different radicals, for example by 1 to 5, preferably 1 to 3, substituents.

The following are suitable substituents for $R^1$ when it is $C_7$–$C_{16}$aralkyl and for $R^2$ and $R^3$ when they are $C_6$–$C_{12}$aryl and $C_7$–$C_{16}$aralkyl: $C_1$–$C_{12}$alkyl, $C_1$–$C_{12}$alkoxy or $C_1$–$C_{12}$alkylthio, preferably $C_1$–$C_6$alkyl, $C_1$–$C_6$alkoxy or $C_1$–$C_6$alkylthio and particularly $C_1$–$C_4$alkyl, $C_1$–$C_4$alkoxy or $C_1$–$C_4$alkylthio, for example methyl, ethyl, propyl, n-, iso- and t-butyl, the isomers of pentyl, hexyl, octyl, nonyl, decyl, undecyl and dodecyl, and corresponding alkoxy and alkylthio radicals; $C_1-C_6$halogenoalkyl, preferably $C_1-C_4$halogenoalkyl, in which halogen is preferably F and Cl, for example trifluoromethyl, trichloromethyl, difluorochloromethyl, fluorodichloromethyl, 1,1-difluoroeth-1-yl, 1,1-dichloroeth1-yl, 1,1,1-trichloroeth-2-yl, 1,1,1-trifluoroeth-2-yl, pentachloroethyl, pentafluoroethyl, 1,1,1-trifluoro-2,2-dichloroethyl, n-perfluoropropyl, iso-perfluoropropyl, n-perfluorobutyl, fluoromethyl, chloromethyl, difluoromethyl, dichloromethyl, 1-fluoroeth-2-yl, 1-chloroeth-2-yl, 1-chloroeth-1-yl, 1-, 2- or 3-fluoroprop-1-yl, 1-, 2- or 3-fluoroprop-2-yl, 1-, 2- or 3-fluoroprop-3-yl, 1-, 2- or 3-chloroprop-2yl, 1-, 2- or 3-chloroprop-3yl, 1-fluorobut-1-yl, -2-yl, -3-yl or -4-yl, 1-chlorobut-1-yl, -2-yl, -3-yl or -4-yl, 2,3-dichloroprop-1-yl, 1-chloro-2-fluoroprop-3-yl or 2,3-dichlorobut-1-yl; halogen, preferably F and Cl; $C_1-C_{12}$aryl, $C_6-C_{12}$aryloxy or $C_6-C_{12}$arylthio in each of which aryl is preferably naphthyl and especially phenyl, $C_7-C_{16}$aralkyl, $C_7-C_{16}$aralkoxy and $C_7-C_{16}$aralkylthio in each of which the aryl radical is preferably naphthyl and especially phenyl and the alkylene radical is linear or branched and contains 1 to 10, preferably 1 to 6 and especially 1–3, C atoms, for example benzyl, naphthylmethyl, 1-phenyleth-1-yl, 1-phenyleth-2-yl, 2-phenyleth-1-yl, 2-phenyleth-2-yl, 1-, 2- or 3-phenylprop-1-yl, 1-, 2- or 3-phenylprop-2-yl or 1-, 2- or 3-phenylprop-3-yl, benzyl being particularly preferred; the abovementioned radicals containing aryl groups can, in turn, be monosubstituted or polysubstituted, for example by $C_1-C_4$alkyl, $C_1-C_4$alkoxy, $C_1-C_4$alkylthio, halogen, —OH, —CN, —CONR$^4$R$^5$ or —COOR$^4$, R$^4$ and R$^5$ being as defined; examples are methyl, ethyl, n-propyl, isopropyl, butyl, corresponding alkoxy and alkylthio radicals, F, Cl, Br, dimethylcarbamoyl, methylethylcarbamoyl, diethylcarbamoyl, methoxycarbonyl, ethoxycarbonyl, phenoxycarbonyl and benzyloxycarbonyl; secondary amino having 2 to 24, preferably 2 to 12 and especially 2 to 6, C atoms, the secondary amino preferably containing 2 alkyl groups, for example dimethylamino, methylethylamino, diethylamino, methyl-n-propylamino, methyl-n-butylamino, di-n-propylamino, di-n-butylamino or di-n-hexylamino; —CONR$^4$R$^5$ in which R$^4$ and R$^5$ independently of one another are $C_1-C_{12}$alkyl, preferably $C_1-C_6$alkyl and especially $C_1-C_4$alkyl, or R$^4$ and R$^5$ together are tetramethylene, pentamethylene or 3-oxapentylene, it being possible for the alkyl to be linear or branched, for example dimethylcarbamoyl, methylethylcarbamoyl, diethylcarbamoyl, methyl-n-propylcarbamoyl, ethyl-n-propylcarbamoyl, di-n-propylcarbamoyl, methyl-n-butylcarbamoyl, ethyl-n-butylcarbamoyl, n-propyl-n-butylcarbamoyl and di-n-butylcarbamoyl; —COOR$^4$ in which R$^4$ is $C_1-C_{12}$alkyl, preferably $C_1-C_6$alkyl, which can be linear or branched, for example methyl, ethyl, n-propyl, isopropyl, n-, iso- and t-butyl and the isomers of pentyl, hexyl, heptyl, octyl, nonyl, decyl, undecyl and dodecyl.

As alkyl substituted by heteroaryl, R$^1$ is preferably derived from a 5-membered or 6-membered ring which has 1 or 2 identical or different heteroatoms, especially O, S or N, and which preferably contains 4 or 5 C atoms and can be condensed with benzene. Examples of heteroaromatic compounds are furan, pyrrole, thiophene, pyridine, pyrimidine, indole and quinoline.

As heterocycloalkyl or as alkyl substituted by heterocycloalkyl, R$^1$ preferably contains 4 to 6 ring atoms and 1 or 2 identical or different heteroatoms selected from the group consisting of O, S and NR$^4$. It can be condensed with benzene. It can be derived, for example, from pyrrolidine, tetrahydrofuran, tetrahydrothiophene, indane, pyrazolidine, oxazolidine, piperidine, piperazine or morpholine.

The same preferences as for the substituents of R$^1$ apply to the substituents of R$^2$ and R$^3$. As alkyl, R$^1$, R$^2$ and R$^3$ are preferably unsubstituted or substituted $C_1-C_6$alkyl, especially $C_1-C_4$alkyl, which can be linear or branched. Examples are methyl, ethyl, isopropyl, n-propyl, iso-, n- and t-butyl and the isomers of pentyl, hexyl, heptyl, octyl, nonyl, decyl, undecyl and dodecyl.

As unsubstituted or substituted cycloalkyl, R$^1$, R$^2$ and R$^3$ preferably contain 3 to 6, especially 5 or 6, ring C atoms. Examples are cyclopropyl, cyclobutyl, cyclopentyl, cyclohexyl, cycloheptyl and cyclooctyl.

As aryl, R$^2$ and R$^3$ are preferably unsubstituted or substituted naphthyl and especially unsubstituted or substituted phenyl. As aralkyl, R$^1$, R$^2$ and R$^3$ are preferably unsubstituted or substituted phenylalkyl having 1–10, preferably 1 to 6 and especially 1 to 4, C atoms in the alkylene, it being possible for the alkylene to be linear or branched. Parti-cular examples are benzyl and 1-phenyleth-1-yl, 2-phenyleth-1-yl, 1-phe-nylprop-1-yl, 1-phenylprop-2-yl, 1-phenylprop-3-yl, 2-phenylprop-1-yl, 2-phenylprop-2-yl and 1-phenylbut-4-yl.

When R$^2$ and R$^3$ are —CONR$^4$R$^5$ and —COOR$^4$, R$^4$ and R$^5$ are preferably $C_1-C_6$alkyl, especially $C_1-C_4$alkyl, or R$^4$ and R$^5$ together are tetramethylene, pentamethylene or 3-oxapentylene. Examples of alkyl have been mentioned above.

When R$^2$ and R$^3$ together, or R$^1$ and R$^3$ together, are alkylene, they are preferably interrupted by 1 —O—, —S— or —NR$^4$—, preferably —O— group. Together with the C atom or with the —N═C— group to which they are attached, R$^2$ and R$^3$ jointly, or R$^1$ and R$^3$ jointly, preferably form a 5-membered or 6-membered ring. The preferences mentioned above apply to the substituents, $C_1-C_4$alkyl being suitable in addition as a substituent. As condensed alkylene, R$^2$ and R$^3$ together, or R$^1$ and R$^3$ together, are preferably alkylene which is condensed with benzene or pyridine. The following are examples of alkylene: ethylene, 1,2-propylene, 1,3-propylene, 1,2-, 1,3- or 1,4-butylene, 1,5-pentylene and 1,6-hexylene. Examples of alkylene which is interrupted or substituted by ═O are 2-oxa1,3-propylene, 2-oxa-1,4-butylene, 2-oxa-1,5-pentylene, 3-oxa-1,5-pentylene, 3-thia-1,5-pentylene, 2-thia-1,4-butylene, 2-thia-1,3-propylene, 2-methylimino-1,3-propylene, 2-ethylimino-1,4-butylene, 2-methylimino-1,5-pentylene, 3-methylimino-1,5-pentylene, 1-oxo-2-oxa-1,3-propylene, 1-oxo2-oxa-1,4-butylene, 2-oxo-3-oxa-1,4-butylene and 1-oxa-2-oxo-1,5-pentylene. The following are examples of condensed alkylene:

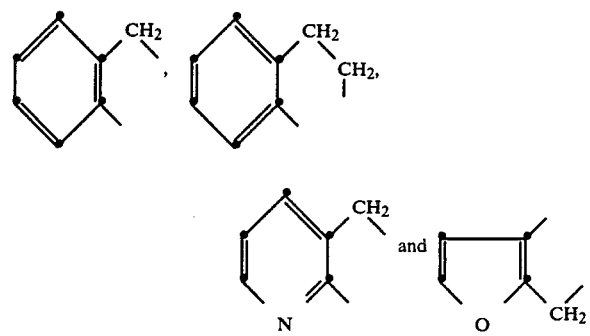

The following are examples of condensed and interrupted alkylene which is unsubstituted or substituted by =O:

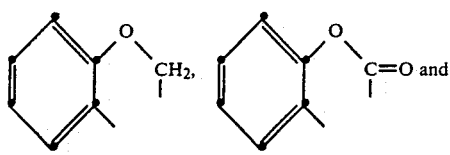

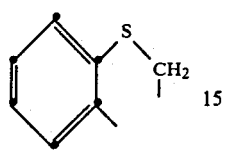

In a preferred group, R¹ is (methoxycarbonyl)-methyl and R² and R³ together are the radical of the formula

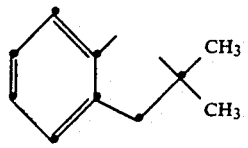

Imines of the formula II are known or can be prepared by known processes from ketones and corresponding amines. In one embodiment of the process the imines of the formula II can also be prepared in situ from the corresponding ketones and amines.

The process is preferably carried out at a temperature from −20° to 50° C., in particular −20° to 30° C. and especially −20° to 20° C., and preferably under a hydrogen pressure of $2\times10^5$ to $6\times10^6$ Pa, in particular $8\times10^5$ to $6\times10^6$ Pa.

In the formulae III and IIIa, X as an olefin ligand can be, for example, butene, propene and especially ethylene, and the diene ligand is preferably an open-chain or cyclic diene the double bonds of which are attached through one or two C atoms. The diene is preferably hexadiene, cyclooctadiene or norbornadiene.

In the chiral diphosphine, the phosphine groups are preferably attached via an aliphatic group which has 2-C atoms and can be substituted by $C_1$-$C_4$alkyl, $C_5$cycloalkyl, $C_6$cycloalkyl, phenyl or benzyl. The aliphatic group can be alkylene or a cycloaliphatic group having 5 or 6 ring C atoms or an aliphatic-heterocyclic group having 1 to 2 —O— or =N— $C_1$-$C_{12}$alkyl, =N—$C_1$-$C_{12}$acyl, =N—$C_1$-$C_{12}$aminocarbonyl, =N—$C_1$-$C_{12}$phenyl or =N—$C_1$-$C_{12}$benzyl group and 3–5 C atoms in the ring. The rings can be substituted by $C_1$-$C_4$alkyl, $C_5$-$C_7$cycloalkyl, phenyl or benzyl.

Y in the formula III or IIIa is preferably a chiral diphosphine the phosphine groups of which are attached to 4 C atoms and which, together with the Ir atom, forms a 7-membered ring.

The phosphine groups and phosphinite groups preferably contain $C_1$-$C_{12}$alkyl, cycloalkyl which has 5 to 8 ring C atoms and can be substituted by 1 to 3 $C_1$-$C_6$alkyl groups, phenyl, $C_7$-$C_{12}$phenylalkyl or alkylphenylalkyl having 1 to 6 C atoms in the alkyl groups and 1 to 5 C atoms in the alkylene group. t-Butyl, phenyl, benzyl or cyclohexyl are particularly preferred. Suitable chiral diphosphines are described in H. B. Kagan, Chiral Ligands for Asymmetric Catalysis, Asymmetric Synthesis, volume 5, pages 13–23, Academic Press, Inc., N.Y. (1985).

The following are examples (Ph is phenyl):

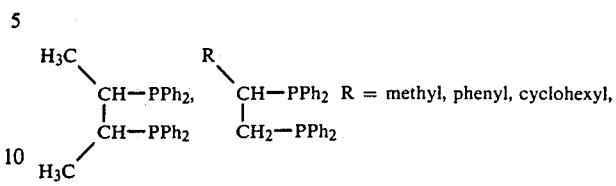

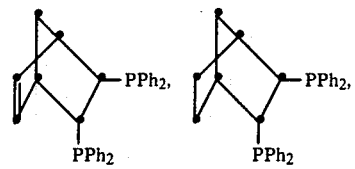

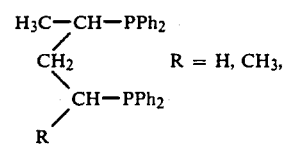

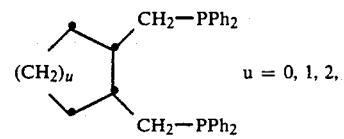

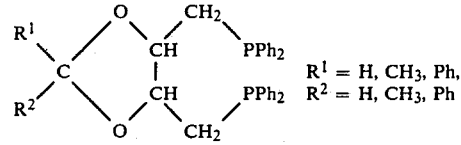

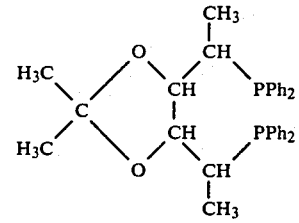

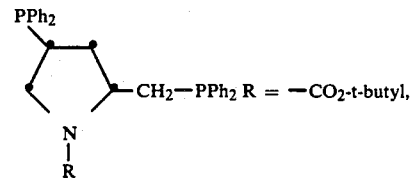

—CO-t-butyl, —CONHC₁-C₄-alkyl,

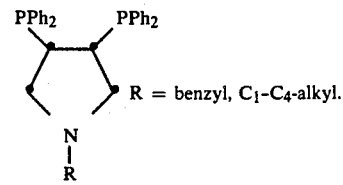

1-O-Phenyl-4,6-O-(R)-benzylidene-2,3-O-bis(diphenylphosphino)-β-D-glucopyranoside of the formula

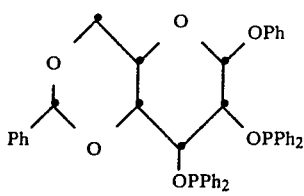

is an example of diphosphinites.

In formula III Z is preferably Cl or Br. A⊖ in formula IIIa is preferably ClO₄⊖, CF₃SO₃⊖, BF₄⊖, B(phenyl)₄⊖, PF₆⊖, SbCl₆⊖, AsF₆⊖ or SbF₆⊖.

A preferred group of iridium compounds is formed by those of the formula III in which X is cyclooctadiene, Z is Cl and Y is chiral diphosphines.

The iridium compounds of the formulae III and IIIa are known or can be prepared by known processes, see, for example, R. Uson et al., Inorg. Chim. Acta 73, pages 275 et seq. (1983); S. Brunie et al., Journal of Organometallic Chemistry, 114 (1976), pages 225-235 and M. Green et al., J. Chem. Soc. (A), pages 2334 et seq. (1971).

The iridium compounds can be employed in the form of isolated compounds. It is advantageous to prepare the compounds in situ and to use them without further treatment.

It is preferable to employ the iridium compounds in amounts of 0.01 to 5, particularly 0.05 to 2, mol %, relative to the compounds of the formula II. The molar ratio of compound of the formula II to compound of the formula III or IIIa is preferably between 500 and 40, particularly between 200 and 50.

A preferred procedure for the process comprises using in addition an ammonium chloride, bromide or iodide or an alkali metal chloride, bromide or iodide. The addition of chlorides, bromides or iodides is particularly advantageous when compounds of the formula IIIa are employed as catalysts. The chlorides, bromides and iodides can be employed, for example, in amounts of 0.1 to 100, preferably 1 to 50 and very preferably 2 to 20, equivalents, relative to the compounds of the formula III or IIIa. The iodides are the preferred salts. Ammonium is preferably tetraalkylammonium having 1 to 6 C atoms in the alkyl groups, and the alkali metal is preferably sodium, lithium or potassium.

The reaction can be carried out without solvents or in the presence of solvents. The following are examples of suitable solvents, which can be employed on their own or as a mixture of solvents: aliphatic and aromatic hydrocarbons, for example pentane, hexane, cyclohexane, methylcyclohexane, benzene, toluene and xylene; alcohols, for example methanol, ethanol, propanol and butanol; ethers, for example diethyl ether, diethylene glycol dimethyl ether, tetrahydrofuran and dioxane; halogenated hydrocarbons, for example methylene chloride, chloroform, 1,1,2,2-tetrachloroethane and chlorobenzene; esters and lactones, for example ethyl acetate, butyrolactone and valerolactone; and N-substituted acid amides and lactams, for example dimethylformamide, dimethylacetamide and N-methylpyrrolidone. Mixtures of an aromatic hydrocarbon and alcohols, for example toluene/ ethanol or benzene/methanol, are advantageous.

The compounds of the formula I are intermediates for the preparation of biologically active substances, particularly in the sector of pharmaceuticals and agrochemicals. Thus it is possible to prepare from the secondary amines, in particular, N-carboalkoxymethylamines and 5-imidazolecarboxylic acid derivatives which have a herbicidal action and can be used for the control of weeds (cf. EP-A 0,207,563).

The following examples illustrate the invention in greater detail.

EXAMPLE 1

10 mmol of ketimine are introduced into a 250 ml two-necked flask under argon as a protective gas. The flask is evacuated and flushed with nitrogen three times. 5 ml of methanol and 5 ml of benzene are then added and the mixture is stirred for 2 minutes at room temperature (solution A).

5 ml of methanol and 5 ml of benzene are introduced into a 25 ml two-necked flask under argon as a protective gas. 0.1 mmol of [Ir-(cyclooctadiene)-Cl]₂, 0.22 mmol of diphosphine and, where indicated, 0.4 mmol of tetrabutylammonium iodide (TBAI) are then added successively. After each addition the mixture is stirred until a homogeneous solution is present (solution B).

The solutions A and B are introduced successively, with the exclusion of air, into a 120 ml glass autoclave or a 65 ml steel autoclave. Hydrogen is injected to $2 \times 10^6$ Pa through a gas inlet valve. At the same time hydrogen is injected to $1.4 \times 10^7$ into a 100 ml reservoir. The temperature is 20°–22° C. The reaction is carried out under a constant hydrogen pressure of $2 \times 10^6$ Pa until no further absorption of hydrogen takes place. The reaction mixture is then flushed by means of nitrogen into a 250 ml flask. The solvent is removed on a rotary evaporator at 80° C. This gives a crude product, which is distilled in a high vacuum (1–10 Pa). The optical yield is then determined by polarimetry (A. F. Lee et al., J. Chem. Arc. 1954, 145) or by means of ¹H-NMR using shift reagents, or by means of HPLC using a column containing (R)-dinitrobenzoylphenylglycine covalent.

The optical yields (ee in %), the reaction times and the conversion are shown in Table 1.

TABLE 1

| Ketimine | Conversion (%) | Reaction time (hours) | Optical yield (% ee) |
|---|---|---|---|
| (structure) | 99 | 1,8 | 23,4 |

TABLE 1-continued
| Ketimine | Conversion (%) | Reaction time (hours) | Optical yield (% ee) |
|---|---|---|---|
| 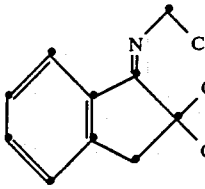 | 99 | 22 | 23,4 |
| 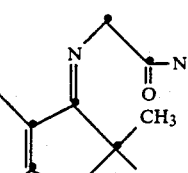 | 53 | 75 | 26,4 |
| 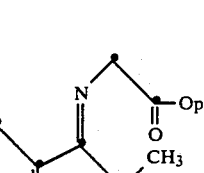 | 98 | 7 | 10 |
| 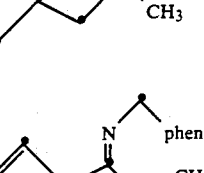 | 99 | 7 | 23 |
| 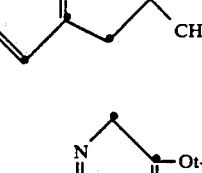 | 40 | 22,5 | 26 |
| 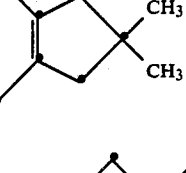 | 99 | 2,3 | 16,5 |
| 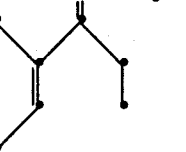 | 99 | 1 | 16 |

TABLE 1-continued

| Ketimine | Conversion (%) | Reaction time (hours) | Optical yield (% ee) |
|---|---|---|---|
| (cyclohexyl phenyl ketimine with propyl N-substituent) | 99 | 0,5 | 18 |
| (phenyl methyl ketimine, N-CH2-phenyl) | 99 | 5 | 30 |
| (tert-butyl methyl ketimine, N-propyl) | 99 | 0,5 | 8 |
| (3,4-dimethoxybenzyl, C6H5) | 38 | 21,5 | 5 |
| (3,4-dimethoxybenzyl, CH2C5H6) | 96 | 69 | 29 |
| (dimethyl-substituted indane imine) | 40 | 22 | 15 |

(*) 20 mMol (1) 6.5 mmol

Catalyst: [Ir-(cyclooctadiene)-Cl]₂ and (−)-DIOP.
Additive: 2 equivalents of TBAI, relative to the catalyst.
Determination of % ee: by means of HPLC or ¹H-NMR spectroscopy.

EXAMPLE 2

The procedure of Example 1 is repeated, using various diphosphines. The following is used as the ketimine:

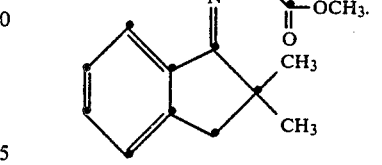

The results are shown in Table 2.

TABLE 2

| Diphosphine | Conversion (%) | Reaction time (hours) | Optical yield (% ee) | Configuration |
|---|---|---|---|---|
|  (CHIRAPHOS) | 81 | 65 | 16 | S |
| 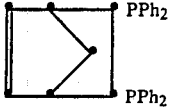 [(+)-NORPHOS] | 86 | 22,5 | 4 | R |
| 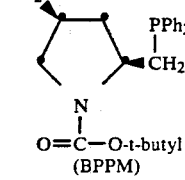 (BPPM) | 95 | 0,4 | 29,5 | R |
| 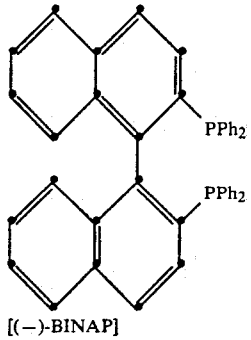 [(−)-BINAP] | 83 | 17,5 | 19,6 | S |
| 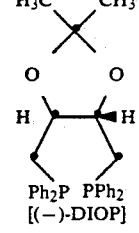 [(−)-DIOP] | 99 | 1,8 | 23,4 | R |
| 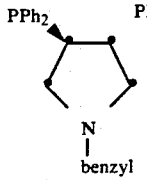 benzyl | 99 | 5 | 24 | S |

Ketimine: catalyst molar ratio = 50:1
Catalyst: [Ir-(cyclooctadiene)-Cl]$_2$ and 2.2 equivalents of diphosphine
Additive: 2 equivalents of TBAI, relative to the catalyst
Determination of % ee: by means of HPLC.

EXAMPLE 3

The procedure of Example 1 is repeated, varying the reaction conditions. The results are collated in Table 3.

TABLE 3

| Additive (equivalents of TBAI) | Solvent | Pressure ($10^6$ Pa) | Temperature (°C.) | Conversion (%) | Reaction Time (hours) | Optical yield (% ee) | Configuration |
|---|---|---|---|---|---|---|---|
| 2 | Methanol/Benzene | 20 | 20 | 99 | 1 | 23,4 | R |

TABLE 3-continued

| Additive (equivalents of TBAI) | Solvent | Pressure ($10^6$ Pa) | Temperature (°C.) | Conversion (%) | Reaction Time (hours) | Optical yield (% ee) | Configuration |
|---|---|---|---|---|---|---|---|
| 10 | Methanol/Benzene (1:1) | 20 | 20 | 99 | 2 | 22,0 | R |
| 2 | Methanol/Benzene (1:1) | 20 | 50 | 99 | 0,5 | 21,7 | R |
| 2 | Methanol/Benzene (1:1) | 20 | 0 | 99 | 4 | 25,0 | R |
| 2 | Methanol/Benzene (1:1) | 10 | 20 | 99 | 6 | 23,0 | R |
| 2 | Methanol/Benzene (1:1) | 50 | 20 | 99 | 1 | 22,6 | R |
| 2 | Tetrahydrofuran | 20 | 20 | 99 | 4 | 19 | R |
| — | " | 20 | 20 | 92 | 22 | 3,5 | S |
| — | Methanol | 20 | 20 | 62 | 22,5 | 2 | R |
| — | Methylenechloride | 20 | 20 | 97 | 20 | 9 | S |
| 2 | Dimethylformamide | 20 | 20 | 91 | 18 | 8,5 | R |
| — | " | 20 | 20 | 99 | 21 | 4 | S |

Ketimine according to example 2
Catalyst according to example 1
Molar ratio ketimine:catalyst = 50

What is claimed is:

1. A process for the preparation of optically active secondary N-aliphatic amines of the formula I

in which $R^1$ is linear or branched $C_1$-$C_{12}$alkyl, cycloalkyl having 3 to 8 ring C atoms, heterocycloalkyl which is linked via a C atom and has 3 to 8 ring atoms and 1 or 2 heteroatoms selected from the group consisting of O, S and $NR^4$, a $C_7$-$C_{16}$aralkyl or $C_1$-$C_{12}$alkyl which is substituted by the cycloalkyl or heterocycloalkyl or heteroaryl mentioned each of which can be unsubstituted or substituted by $C_1$-$C_{12}$alkyl, $C_1$-$C_{12}$alkoxy, $C_1$-$C_{12}$alkylthio, $C_1$-$C_6$halogenoalkyl, halogen, —OH, —CN, $C_6$-$C_{12}$aryl, $C_6$-$C_{12}$aryloxy, $C_6$-$C_{12}$arylthio, $C_7$-$C_{16}$aralkyl, $C_7$-$C_{16}$aralkoxy or $C_7$-$C_{16}$aralkylthio, it being possible for the aryl radicals in turn to be substituted by $C_1$-$C_4$—alkyl, $C_1$-$C_4$alkoxy, $C_1$-$C_4$alkylthio, halogen, —OH, —CN, —$CONR^4R^5$ or —$COOR^4$, secondary amino having 2 to 24 C atoms,

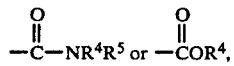

$R^5$ being H or independently being as defined for $R^4$ and $R^4$ being $C_1$-$C_{12}$alkyl, phenyl or benzyl, or $R^4$ and $R^5$ together being tetramethylene, pentamethylene or 3-oxapentylene; $R^2$ and $R^3$ are different from one another and are $C_1$-$C_{12}$alkyl which is unsubstituted or substituted by —OH, —CN, halogen, $C_1$-$C_{12}$alkoxy, benzyloxy, secondary amino having 2 to 24 C atoms,

or —$COOR^4$, or are cycloalkyl having 3-8 ring C atoms, $C_6$-$C_{12}$aryl which is unsubstituted or substituted as above for $R^1$ where the latter is aralkyl and aryl, or $C_7$-$C_{16}$aralkyl or —$CONR^4R^5$ or —$COOR^4$ in which $R^4$ and $R^5$ are as defined above; or $R^1$ is as defined above and $R^2$ and $R^3$ together are alkylene which has 2 to 5 C atoms and is, if appropriate, interrupted by 1 or 2 —O—, —S— or —$NR^4$— groups, and/or is unsubstituted or substituted by =O or as above for $R^2$ and $R^3$ when the latter are alkyl, and/or is condensed with benzene, furan, thiophene or pyrrole which is unsubstituted or substituted as mentioned above for the aryl radicals, or $R^2$ is as defined above and $R^1$ and $R^3$ together are alkylene which has 2 to 5 C atoms and is, if appropriate, interrupted by 1 or 2 —O—, —S— or —$NR^4$— groups, and/or is unsubstituted or substituted by =O or as above for $R^2$ and $R^3$ when the latter are alkyl, and/or is condensed with benzene, furan, thiophene or pyrrole which is unsubstituted or substituted as defined above, and * is predominant R-configuration or S-configuration, by the asymmetric catalysed hydrogenation of prochiral ketimines of the formula II

in which $R^1$, $R^2$ and $R^3$ are as defined above, in the presence of complex salts of a noble metal having chiral ligands, which comprises carrying out the hydrogenation at a temperature from $-20°$ to 80° C. and under a hydrogen pressure from $10^5$ Pa to $10^7$ Pa and adding to the reaction mixture catalytic amounts of an iridium compound of the formula III or IIIa

[XIrYZ]  (III)

or

[XIrY]⊕A⊖  (IIIa)

in which X is two olefin ligands or a diene ligand, Y is a chiral diphosphine the secondary phosphine groups of which are attached through 2-4 C atoms and which, together with the Ir atom, forms a 5-membered, 6-membered or 7-membered ring, or Y is a chiral diphosphinite the phosphinite groups of which are attached via 2 C atoms and which, together with the Ir atom, forms a 7-membered ring, Z is Cl, Br or I and A⊖ is the anion of an oxygen acid or complex acid.

2. A process according to claim 1, wherein the reaction temperature is $-20°$ to 50° C.

3. A process according to claim 1, wherein the hydrogen pressure is $2 \times 10^5$ Pa to $6 \times 10^6$ Pa.

4. A process according to claim 1, wherein X in the formulae III and IIIa is two ethylene groups or an open-chain or cyclic diene the double bonds of which are attached via 1 or 2 C atoms.

5. A process according to claim 4, wherein the diene is hexadiene, norbornadiene or cyclooctadiene.

6. A process according to claim 1, wherein Y in the formulae III and IIIa is a chiral diphosphine the phosphine groups of which are attached through 4 C atoms and which, together with the Ir atom, forms a 7 ring.

7. A process according to claim 1, wherein the phosphine and phosphinite groups contain $C_1$-$C_{12}$alkyl, cycloalkyl which has 5 to 8 ring C atoms and can be substituted by 1 to 3 $C_1$-$C_6$alkyl groups, phenyl, $C_7$-$C_{12}$phenylalkyl or alkylphenylalkyl having 1 to 6 C atoms in the alkyl groups and 1 to 5 C atoms in the alkylene group.

8. A process according to claim 1, wherein $A\ominus$ is $ClO_4\ominus$, $CF_3SO_3\ominus$, $BF_4\ominus$, $B(phenyl)_4\ominus$, $PF_6\ominus$, $SbCl_6\ominus$, $AsF_6\ominus$ or $SbF_6\ominus$.

9. A process according to claim 1, wherein the iridinium compound is added in an amount of 0.01 to 5 mol %, relative to the compound of the formula II.

10. A process according to claim 1, wherein, in addition, an ammonium chloride, bromide or iodide or an alkali metal chloride, bromide or iodide is added.

11. A process according to claim 1, wherein, in formula III, X is cyclooctadiene, Z is Cl and Y is a chiral diphosphine.

* * * * *